(12) United States Patent
Corradi

(10) Patent No.: US 10,287,512 B2
(45) Date of Patent: *May 14, 2019

(54) PROCESS AND APPARATUS FOR DESORBENT RECOVERY

(71) Applicant: UOP LLC, Des Plaines, IL (US)

(72) Inventor: Jason T. Corradi, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/997,873

(22) Filed: Jun. 5, 2018

(65) Prior Publication Data

US 2019/0002769 A1    Jan. 3, 2019

Related U.S. Application Data

(60) Provisional application No. 62/526,920, filed on Jun. 29, 2017.

(51) Int. Cl.
*C10G 25/12* (2006.01)
*C10G 7/12* (2006.01)
*B01D 3/14* (2006.01)

(52) U.S. Cl.
CPC .............. *C10G 25/12* (2013.01); *B01D 3/143* (2013.01); *C10G 7/12* (2013.01); *C10G 2300/1096* (2013.01); *C10G 2300/4006* (2013.01); *C10G 2400/30* (2013.01)

(58) Field of Classification Search
CPC ........... C07C 7/12; C07C 15/06; C07C 15/08; B01D 3/143
See application file for complete search history.

(56) References Cited

U.S. PATENT DOCUMENTS

| | | | | |
|---|---|---|---|---|
| 8,609,922 B2* | 12/2013 | Werba | ..................... | B01D 3/007 203/25 |
| 2013/0233698 A1* | 9/2013 | Corradi | .................. | B01D 3/143 203/41 |

* cited by examiner

*Primary Examiner* — Brian A McCaig
*Assistant Examiner* — Jason Y Chong

(57) ABSTRACT

The present invention relates to a process and apparatus for reducing the desorbent recovery cost in a light desorbent system. More specifically, the present invention relates to an alternate flow scheme that for pre-fractionation of the extract column feed which includes two extract columns which reduces the desorbent recovery costs in a light desorbent system.

5 Claims, 2 Drawing Sheets

US 10,287,512 B2

PROCESS AND APPARATUS FOR DESORBENT RECOVERY

CROSS-REFERENCE TO RELATED APPLICATION

This application claims priority from Provisional Application No. 62/526,920 filed Jun. 29, 2017, the contents of which cited application are hereby incorporated by reference in its entirety.

FIELD

The present invention relates to a process and apparatus for reducing the desorbent recovery cost in a light desorbent system. More specifically, the present invention relates to an alternate flow scheme that for pre-fractionation of the extract column feed which includes two extract columns which reduces the desorbent recovery costs in a light desorbent system.

BACKGROUND

A process for desorbent recovery is described. Paraxylene production from selective adsorption systems creates raffinate and extract intermediate product streams comprised of desorbent and feed component mixtures. The desorbent can be characterized as either light or heavy to indicate its boiling point relative to the feed constituents. A desorbent recovery system is required to separate the desorbent for recycle. Recovery of light desorbents such as toluene requires energy intensive distillation where the desorbent is recovered as an overhead distillate product.

Toluene has a relatively low dew point temperature compared to a heavy desorbent with higher molecular weight. Therefore, higher condensing pressures are required to meet typical heat recovery temperature approaches within an aromatics complex. Higher pressure column operation is inherently less energy efficient as relative volatilities decrease, as well as more capital intensive as equipment becomes thicker and heavier.

The current approach to desorbent recovery employs a high pressure raffinate column. Operating pressure is high enough to utilize the overhead vapor condensing stream to provide heat input to low pressure column reboilers, including the extract column reboiler. This is a well-established practice yet an unacceptably large amount of heat from desorbent recovery is ultimately rejected to the atmosphere. Therefore, a means of reducing the desorbent recovery costs in a light desorbent system is needed.

SUMMARY

The present invention is a process for desorbent recovery. The invention is an alternate flowscheme that includes pre-fractionation of the extract column feed. A second embodiment (not shown) with pre-fractionation of the raffinate column feed is also contemplated. Prior art did not include these additional columns. The pre-fractionation columns operate at atmospheric pressure so that they provide a heat sink (reboiler duty) for the downstream high pressure column condensing duty. This approach saves energy by eliminating wasteful heat loss to the atmosphere via aircooling. The technical benefits of the invention are realized as reduced operating cost. In the examples provided, a substantial steam export credit equivalent to approximately 10% of the total hot utility consumption can be realized. At some sites, steam may be in surplus and export credit cannot be taken. In those instances, the second example demonstrates how the overall fuel consumption can be reduced by 7% (excluding charge heaters) with no steam export.

DETAILED DESCRIPTION

The following detailed description is merely exemplary in nature and is not intended to limit the application and uses of the embodiment described. Furthermore, there is no intention to be bound by any theory presented in the preceding background or the following detailed description.

Figure 1:
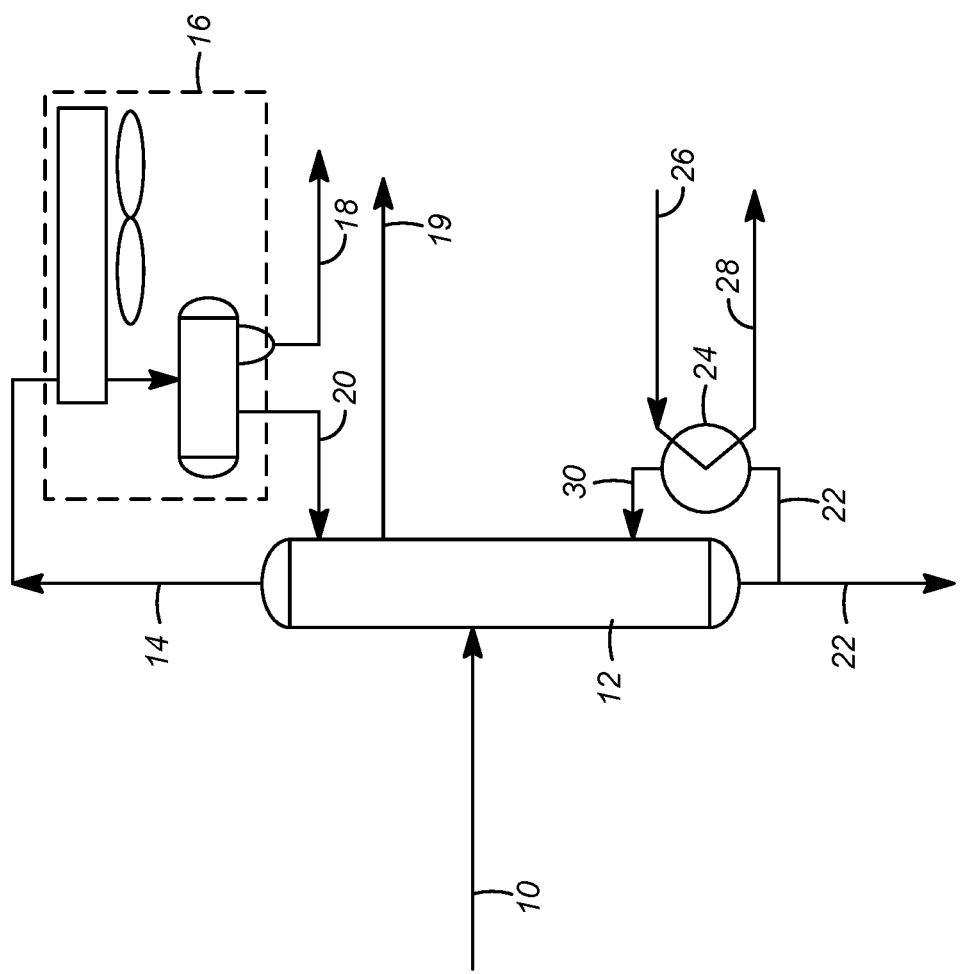
FIG. 1 illustrates the current state of the art for desorbent recovery.
Figure 2:
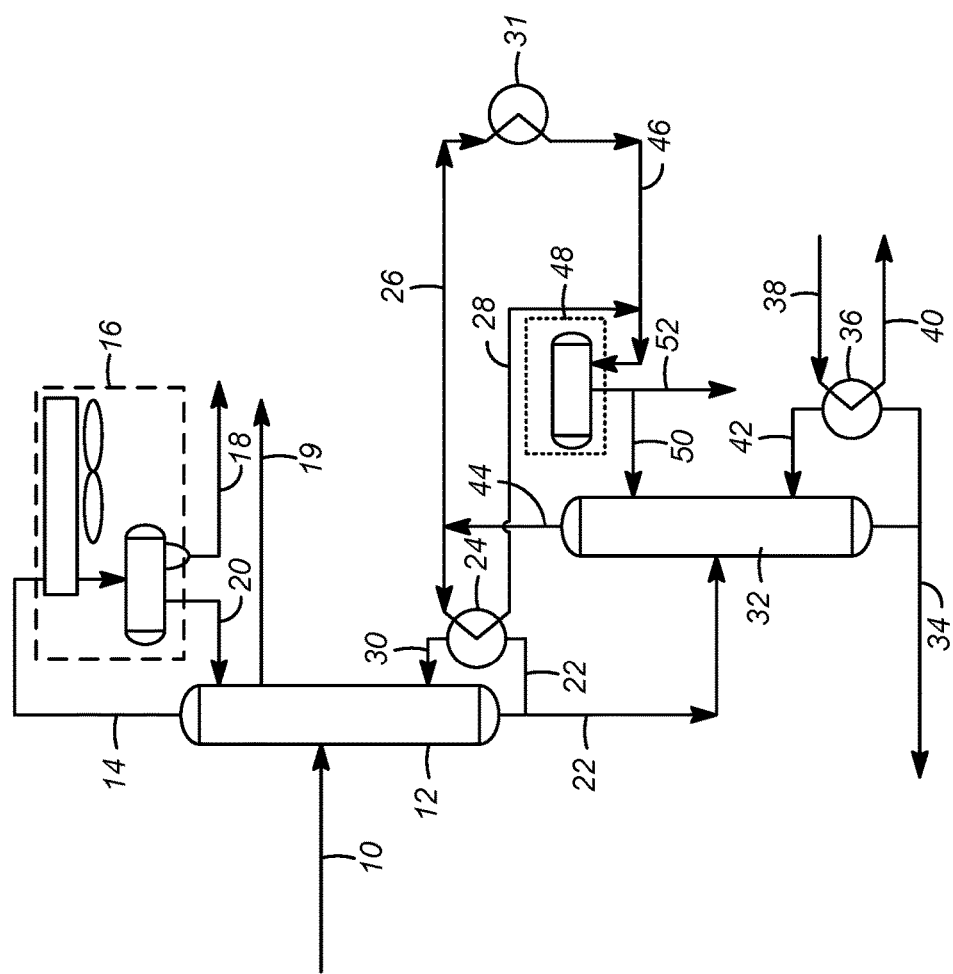
FIG. 2 illustrates a process and apparatus for desorbent recovery that includes pre-fractionation of the extract column feed.

The description of the process of this invention is presented with reference to the attached FIGS. 1 and 2. FIG. 1 is a simplified flow diagram of the prior art. FIG. 2 is a simplified flow diagram of the preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The various embodiments described herein relate to a process and apparatus for desorbent recovery. What is currently done in the state of the art is illustrated in FIG. 1. As show in FIG. 1, an inlet stream 10 comprising toluene desorbent, extracted para-xylene, and some extracted $C_9$-$C_{10}$ is passed to an extract column 12. The first extract column 12 operates at a temperature of 160° C. to about 165° C. and a pressure of about 0.07 barg. The overhead stream 14 comprising toluene and water exits the column 12 and is fed into a condensing and sub-cooling zone 16 which removes the water in stream 18. Stream 20 which comprises toluene is passed back to the column 12. The condensing and sub-cooling zone 16 may contain air, water, or process-cooled exchangers for removing heat from stream 14. A substantially dry toluene stream 19 is removed from the column 12 at a side draw tray location and recycled back to the adsorbent chamber. The bottoms stream 22 comprising toluene, paraxylene, and extracted $C_9$-$C_{10}$ is passed to the para-xylene column feed. A portion of the bottoms stream 22 is passed to a reboiler 24 which receives a vapor stream 26 from a raffinate column and produces a liquid return 28. Stream is returned to the column 12 having a temperature of about 160° C. to about 165° C.

In FIG. 2, there are two extract columns instead of one. Here, an inlet stream 10 comprising toluene desorbent, extracted para-xylene, and some extracted $C_9$-$C_{10}$ is passed to a first extract column 12. The overhead stream 14 comprising toluene and water exits the first column 12 and is fed into a condensing and sub-cooling zone 16 which removes the water in stream 18. Stream 20 which comprises toluene is passed back to the first column 12. The water extraction zone 16 may contain various means of cooling stream 14 as known to those skilled in the art. A substantially dry first desorbent recycle stream 19 is removed from the first column 12 and passed back to the adsorbent chamber. The bottoms stream 22 comprising toluene, paraxylene and extracted $C_9$-$C_{10}$ is passed to the second extract column feed. A portion of the bottoms stream 22 is passed to a first reboiler 24 which receives a vapor stream 26 from the second extract column and produces a liquid return 28. Stream 30 is returned to the first column 12 having a temperature of about 144° C. to about 147 ° C.

The bottoms stream 22 then enters the second extract column 32. The second extract column 32 operates at a temperature of about 200° C. to about 205° C. and a pressure of about 2.5 barg to about 3.0 barg. The bottoms stream 34 is comprising a mixture of para-xylene and extracted $C_9$-$C_{10}$ is passed to the para-xylene column feed. A portion of the bottoms stream 34 is passed to a third reboiler 36 which receives a vapor stream 38 from a raffinate column (not shown) and produces a liquid return 40. Stream 42 is returned to the second extract column 32 having a temperature of about 200° C. to about 205° C.

The overhead 44 is passed to stream 26 which enters the first reboiler 24 and is also passed to the second reboiler 31. The condensed stream 46 leaving the second reboiler 31 is passed to the condensing zone 48 which produces a desorbent stream 50 that is passed back the second column 32 and a second desorbent recycle stream 52 which is recycled back to the adsorbent chamber. It is contemplated that in other embodiments there may be a third extract column.

While the invention has been described with what are presently considered the preferred embodiments, it is to be understood that the invention is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the invention is a process for desorbent recovery, comprising passing a hydrocarbon stream to a first extract column to produce a first overhead stream, a first desorbent recycle stream, and a first bottoms stream; passing the first overhead stream to a first condensing and sub-cooling zone to produce a water stream and a first desorbent reflux stream that is sent back to the first extract column; passing the first desorbent recycle stream to an adsorbent chamber; passing a first portion of the first bottoms stream to a first reboiler and passing a second portion of the first bottoms stream to a second extract column to produce a second overhead stream and a second bottoms stream; passing the second overhead to the first reboiler and a second reboiler to produce a heated stream that produces a second desorbent recycle stream and a second treated desorbent stream that is sent back the second extract column; passing the second overhead to the first reboiler to produce a condensed liquid stream that is sent to a second condensing zone to produce a second desorbent reflux stream and a second desorbent recycle stream; passing the second desorbent reflux stream to the second extract column; passing the second desorbent recycle stream to the adsorbent chamber; passing a first portion of the second bottoms stream to a second reboiler wherein the second reboiler receives a vapor stream from the raffinate column and a liquid return, and passing a second portion of the second bottoms stream to a paraxylene column. An embodiment of the invention is one, any or all of prior embodiments in this paragraph up through the first embodiment in this paragraph, wherein the hydrocarbon stream comprises toluene desorbent, extracted para-xylene, and extracted C9-C10. An embodiment of the invention is one, any or all of prior embodiments in this paragraph up through the first embodiment in this paragraph, wherein the first extract column operates at a temperature of about 160° C. to about 165° C. An embodiment of the invention is one, any or all of prior embodiments in this paragraph up through the first embodiment in this paragraph, wherein the second extract column operates at a pressure of about 0.07 barg. An embodiment of the invention is one, any or all of prior embodiments in this paragraph up through the first embodiment in this paragraph, wherein the second extract column operates at a temperature of about 200° C. to about 205° C. An embodiment of the invention is one, any or all of prior embodiments in this paragraph up through the first embodiment in this paragraph, wherein the second extract column operates at a pressure of about 2.5 barg to about 3.0 barg. An embodiment of the invention is one, any or all of prior embodiments in this paragraph up through the first embodiment in this paragraph, wherein the first desorbent is a heavy desorbent. An embodiment of the invention is one, any or all of prior embodiments in this paragraph up through the first embodiment in this paragraph, wherein the first desorbent is a light desorbent. An embodiment of the invention is one, any or all of prior embodiments in this paragraph up through the first embodiment in this paragraph, wherein the second desorbent is a heavy desorbent. An embodiment of the invention is one, any or all of prior embodiments in this paragraph up through the first embodiment in this paragraph, wherein the second desorbent is a light desorbent.

A second embodiment of the invention is an apparatus for desorbent recovery, comprising; a line for introducing a hydrocarbon stream to a first column from an adsorbent chamber; a first extract column having a first column extract line in direct communication with a condensing and sub-cooling zone, a second column extract line, and a third column extract line in direct communication with a second extract column; and a second extract column having a second column extract line in direct communication with a first reboiler, a second column extract line in direct communication with a second reboiler, and a third column extract line in direct communication with a third reboiler. An embodiment of the invention is one, any or all of prior embodiments in this paragraph up through the second embodiment in this paragraph, wherein the first extract column uses a heavy desorbent. An embodiment of the invention is one, any or all of prior embodiments in this paragraph up through the second embodiment in this paragraph, wherein the first extract column uses a light desorbent. An embodiment of the invention is one, any or all of prior embodiments in this paragraph up through the second embodiment in this paragraph, wherein the second extract column uses a heavy desorbent. An embodiment of the invention is one, any or all of prior embodiments in this paragraph up through the second embodiment in this paragraph, wherein the second extract column uses a light desorbent. An embodiment of the invention is one, any or all of prior embodiments in this paragraph up through the second embodiment in this paragraph, wherein the hydrocarbon stream comprises toluene desorbent, extracted para-xylene, and extracted C9-C10. An embodiment of the invention is one, any or all of prior embodiments in this paragraph up through the second embodiment in this paragraph, wherein the first extract column operates at a temperature of about 144° C. to about 147° C. An embodiment of the invention is one, any or all of prior embodiments in this paragraph up through the second embodiment in this paragraph, wherein the first extract column operates at a and a pressure of about 0.07 barg. An embodiment of the invention is one, any or all of prior embodiments in this paragraph up through the second embodiment in this paragraph, wherein the second extract column operates at temperature of about 200° C. to about 205° C. An embodiment of the invention is one, any or all of prior embodiments in this paragraph up through the second embodiment in this paragraph, wherein the second extract column operates at and a pressure of about 2.5 barg to about 3.0 barg. An embodiment of the invention is one, any or all of prior embodiments in this paragraph up through the second embodiment in this paragraph, wherein a portion of the second column extract line in direct communication with a first reboiler is directed to a para-xylene column feed stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for desorbent recovery, comprising:
    passing a hydrocarbon stream to a first extract column to produce a first overhead stream, a first desorbent recycle stream, and a first bottoms stream, wherein the Hydrocarbon stream comprises toluene desorbent, extracted para-xylene, water, and extracted $C_9$-$C_{10}$;
    passing the first overhead stream to a first condensing and sub-cooling zone to produce a water stream and a first desorbent reflux stream that is sent back to the first extract column;
    passing the first desorbent recycle stream to an adsorbent chamber;
    passing a first portion of the first bottoms stream to a first reboiler and passing a second portion of the first bottoms stream to a second extract column to produce a second overhead stream and a second bottoms stream, wherein the second extract column operates at an elevated pressure compared to the first extract column;
    passing the second overhead stream to the first reboiler to produce a first condensed stream and a second reboiler to produce a second condensed stream;
    passing the first condensed stream and the second condensed stream to a second condensing zone to produce a second desorbent reflux stream and a second desorbent recycle stream;
    passing the second desorbent reflux stream to the second extract column;
    passing the second desorbent recycle stream to the adsorbent chamber; and
    passing a first portion of the second bottoms stream to a third reboiler wherein the third reboiler receives a vapor stream from a raffinate column and produces a liquid return, and passing a second portion of the second bottoms stream to a paraxylene column.

2. The process of claim 1, wherein the first extract column operates at a temperature of about 160° C. to about 165° C.

3. The process of claim 1, wherein the second extract column operates at a pressure of about 0.07 barg.

4. The process of claim 1, wherein the second extract column operates at a temperature of about 200° C. to about 205° C.

5. The process of claim 1, wherein the second extract column operates at a pressure of about 2.5 barg to about 3.0 barg.

* * * * *